US009539072B2

(12) United States Patent
El-Siblani

(10) Patent No.: US 9,539,072 B2
(45) Date of Patent: Jan. 10, 2017

(54) METHOD OF MAKING A DENTAL ARCH MODEL

(71) Applicant: Global Filtration Systems, Dearborn Heights, MI (US)

(72) Inventor: Ali El-Siblani, Dearborn Heights, MI (US)

(73) Assignee: Global Filtration Systems, Dearborn Heights, MI (US)

( * ) Notice: Subject to any disclaimer, the term of this patent is extended or adjusted under 35 U.S.C. 154(b) by 496 days.

(21) Appl. No.: 14/107,396

(22) Filed: Dec. 16, 2013

(65) Prior Publication Data

US 2014/0170591 A1   Jun. 19, 2014

Related U.S. Application Data

(60) Provisional application No. 61/738,120, filed on Dec. 17, 2012.

(51) Int. Cl.
  *B29C 33/44* (2006.01)
  *B29C 35/08* (2006.01)
  (Continued)

(52) U.S. Cl.
  CPC ........... *A61C 13/34* (2013.01); *A61C 13/0004* (2013.01); *A61C 13/0006* (2013.01);
  (Continued)

(58) Field of Classification Search
  CPC ............ A61C 13/0004; A61C 13/0006; A61C 13/0013; A61C 13/0018; A61C 13/0019; A61C 13/34; B29C 33/3835; B29C 33/3842; B29C 33/44; B29C 33/442; B29C 35/08; B29C 35/0805; B29C 2035/0838; B29C 41/02; B29C 67/0051; B29C 67/0055; B29C 67/0059; B29C 67/0062; B29C 67/0066; B29C 67/007; B29C 67/0074; B29C 67/0077; B29C 67/0081; B29C 71/04; B33Y 10/00; B33Y 80/00
  (Continued)

(56) References Cited

U.S. PATENT DOCUMENTS 5,868,569 A    2/1999 Huffman
7,347,690 B2   3/2008 Jordan et al.
(Continued)

OTHER PUBLICATIONS

International Search Report and Written Opinion for PCT/US2013/075350 dated, May 14, 2014.

*Primary Examiner* — Leo B Tentoni
(74) *Attorney, Agent, or Firm* — Hansen IP Law PLLC

(57) ABSTRACT

A dental arch model and method for making the same is shown and described. The dental arch model includes a connector having opposite ends that connect to a respective one of the arch legs. The connector has a three-dimensional shape but does not include a surface that is both planar and parallel to the base of the arch connector along more than two thirds of the arch connector's length. In certain examples, the connector is in the shape of a prism or a trapezoid. In other examples, the connector has an upper surface that is sloped relative to the base of the arch connector. The arch connector may also include a plurality of fluid passageways for allowing fluid flow from an interior area between the inner walls of the arch connector to a location outside of the connector.

8 Claims, 11 Drawing Sheets

(51) Int. Cl.
  *B29C 41/02* (2006.01)
  *A61C 13/34* (2006.01)
  *B29C 67/00* (2006.01)
  *B29C 33/38* (2006.01)
  *A61C 13/00* (2006.01)

(52) U.S. Cl.
  CPC ...... *A61C 13/0013* (2013.01); *A61C 13/0018* (2013.01); *A61C 13/0019* (2013.01); *B29C 33/3835* (2013.01); *B29C 33/3842* (2013.01); *B29C 67/007* (2013.01); *B29C 67/0055* (2013.01); *B29C 67/0059* (2013.01); *B29C 67/0062* (2013.01); *B29C 67/0066* (2013.01); *B29C 67/0074* (2013.01); *B29C 67/0077* (2013.01)

(58) Field of Classification Search
  USPC ............... 264/16, 113, 219, 308, 334, 401, 460,264/461, 462, 463, 482, 494, 496, 497; 433/213; 700/118, 119, 120
  See application file for complete search history.

(56) References Cited

U.S. PATENT DOCUMENTS

| | | | |
|---|---|---|---|
| 7,726,968 B2 | 6/2010 | Raby et al. | |
| 8,215,956 B2 | 7/2012 | Dunne et al. | |
| 8,262,388 B2 | 9/2012 | Dunne et al. | |
| 2001/0012596 A1* | 8/2001 | Kunimoto | A61K 6/083 264/401 X |
| 2001/0042942 A1* | 11/2001 | Hizumi | B29C 67/0066 264/401 |
| 2002/0106584 A1* | 8/2002 | Lawton | G03F 7/0037 264/401 X |
| 2006/0234179 A1 | 10/2006 | Wen et al. | |
| 2007/0031774 A1 | 2/2007 | Cinader, Jr. et al. | |
| 2007/0031791 A1 | 2/2007 | Cinader, Jr. et al. | |
| 2008/0233528 A1* | 9/2008 | Kim | A61C 7/146 433/2 |
| 2008/0233530 A1 | 9/2008 | Cinader | |
| 2010/0217429 A1* | 8/2010 | Kritchman | B29C 67/0055 700/119 |
| 2010/0262272 A1* | 10/2010 | Shkolnik | B29C 67/0088 700/120 |
| 2011/0066267 A1 | 3/2011 | Schmitt | |
| 2012/0258430 A1 | 10/2012 | Ruppert et al. | |
| 2012/0308954 A1 | 12/2012 | Dunne | |

* cited by examiner

METHOD OF MAKING A DENTAL ARCH MODEL

CROSS REFERENCE TO RELATED APPLICATIONS

This application claims the benefit of U.S. Provisional Patent Application No. 61/738,120, filed Dec. 17, 2012, the entirety of which is hereby incorporated by reference.

FIELD

The disclosure relates to dentistry, and more particularly, to dental arch models and methods of making the same.

DESCRIPTION OF THE RELATED ART

Conventional dentistry techniques involve the fabrication of models of the upper and/or lower arches of the teeth for a variety of reasons such as simulating the relative positioning of upper and lower teeth and fabricating crowns or orthodontic appliances. Such known fabrication methods involve, for example, having the patient bite into a pliable material (e.g., alginate or silicone impression material) while it is in a pliable state then hardening the material to yield a semi-flexible impression of the patient's dental arch. Dental gypsum is then poured into the impression and removed from it to create the arch model.

Three-dimensional rapid prototyping and manufacturing can be used for manufacturing dental arch models and in general allows for quick and accurate production of components at high accuracy. In particular, additive three-dimensional rapid prototyping processes may provide a suitable and cost-effective replacement for traditional arch model manufacturing methods. However, known additive processes have certain drawbacks. In particular, it is often necessary to connect the two sides or "legs" of the arch with a connector device so that the legs remain dimensionally stable relative to one another during and following the model manufacturing process. It has been discovered that certain connector geometries may cause variations in solidification depth and layer thickness in the build axis direction during arch manufacturing as well as an undesirable shift in the plane perpendicular to the build axis relative to the object data used to create the arch.

Known three-dimensional rapid prototyping processes employ removable supports that connect the object being built to the build platform on which it is built. The use of such supports minimizes the likelihood of damaging the three-dimensional object upon removal from the build platform on which the object is built. However, the use of supports necessarily wastes solidifiable material and lengthens the time to build the arch model. In addition, when building upper arches, the removal of supports may damage or otherwise disrupt the smoothness of the upper arch's bottom surface. This in turn may make it difficult to align and register the upper arch with the lower arch when connecting the two via an articulator. In addition, certain articulators use pin registration to align all or a portion of upper and lower arch models with one another and the bottom surface of the arch model requires holes that fit with the pins. The use of removable supports can damage or distort the pin holes making the arch unsuitable for pin registration.

The elimination of supports can also be problematic because without supports the model is solidified in direct contact with a build platform which can also cause damage to the arch model upon removal. In addition, trapped volumes of liquid are created within the three-dimensional model during the build process which can result in unwanted sections of cured material and distortions to the model relative to the object data that defines it. Thus, a need has arisen for a dental arch model and method of making the same which addresses the foregoing issues.

BRIEF DESCRIPTION OF THE DRAWINGS

The disclosure will now be described, by way of example, with reference to the accompanying drawings, in which.

Like numerals refer to like parts in the drawings.

DETAILED DESCRIPTION

Figure 1A:
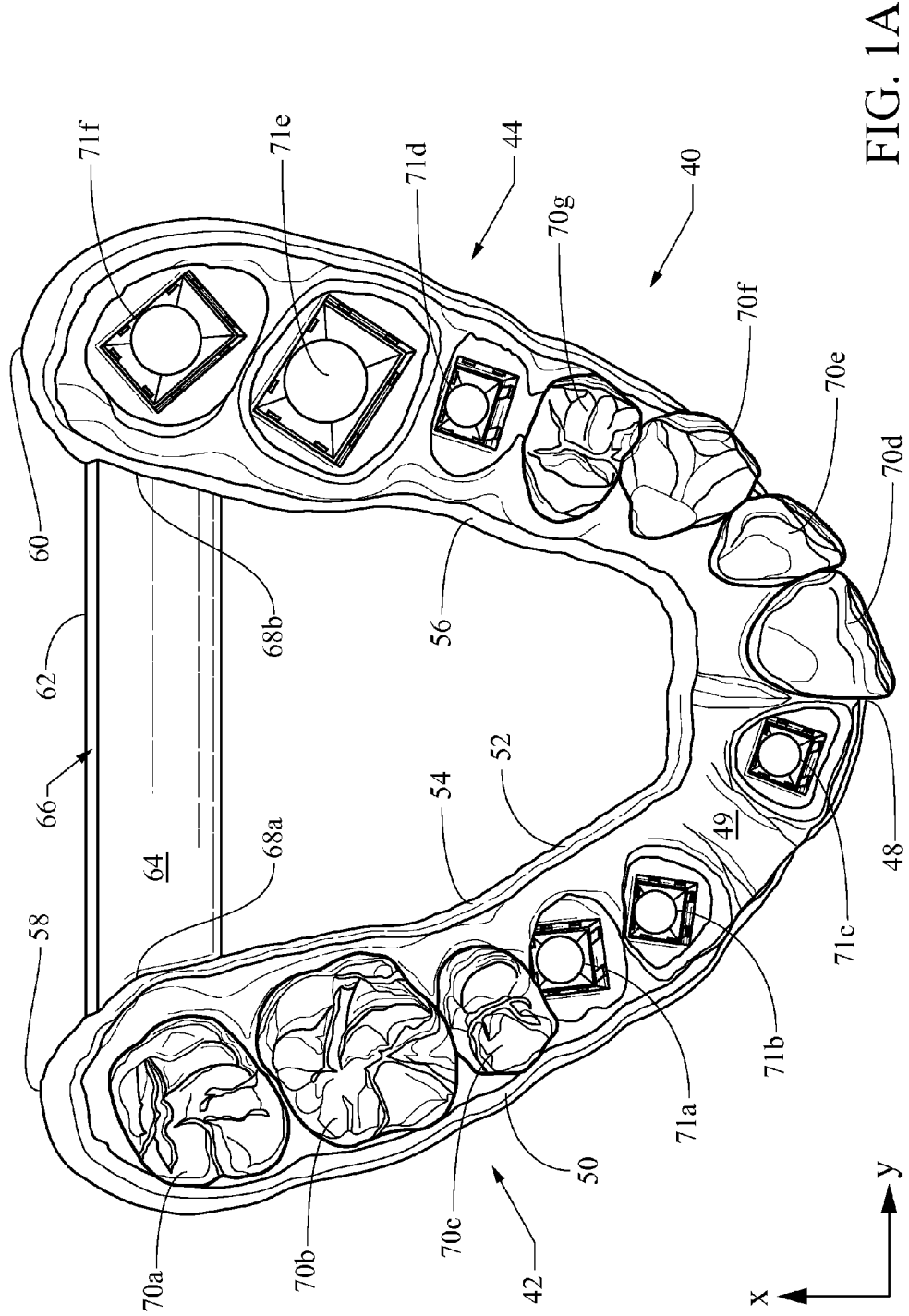
FIG. 1A is top plan view of an embodiment of a dental arch model comprising a prism-shaped connector.

The Figures illustrate examples of various dental arch models including different connectors between the arch legs and/or which include a plurality of fluid passageways. Based on the foregoing, it is to be generally understood that the nomenclature used herein is simply for convenience and the terms used to describe the invention should be given the broadest meaning by one of ordinary skill in the art.

The dental arch models described herein include a connector that connects the two arch legs together. The connector has a lower surface that is substantially parallel to the base of the arch model but preferably does not include a surface that is both substantially parallel to the lower surface and substantially planar along any more than two-thirds of its length. Connectors with this geometry have been found to minimize distortions in the dental arch model that occur with other connector geometries. The dental arch models described herein may also include a plurality of fluid passageways at their base which allow unsolidified material used to form the model to flow from an interior region of the arch model to an exterior region of the arch model.

The apparatuses and methods described herein are generally applicable to additive manufacturing of three-dimensional objects, such as components or parts (discussed herein generally as objects), but may be used beyond that scope for alternative applications. Certain systems used to make the dental arch models described herein are generally described for manufacturing and rapid prototyping, where a pattern generator (such as a DLP device) provides an image to a reactive material for selective hardening. The system may use single or multiple pattern generators. In general, an application of the system and method described herein may use a pattern generator to build a three-dimensional object by exposing a polymerizable material to electromagnetic radiation. The depth of hardening of the polymerizable material may be controlled by the intensity of electromagnetic radiation from the pattern generator at a building plane and/or the exposure time of the building plane to the electromagnetic radiation. Other systems such as photopolymer jet and multi-material photopolymer jet systems may dispense solidifiable material in a desired pattern and then solidify it with unpatterned electromagnetic radiation.

The systems and methods described herein may be used with "downward", "upward" and "side" projecting systems, any of which may include additional optical elements such as a mirror or lenses. They may be used in a layer, slice, or voxelized production process, among others, where the pattern generating system provides the means to react with (e.g., solidify or partially solidify) a photopolymer or other material to create the three-dimensional object. Moreover, the systems and methods described herein may also apply to construction processes using "upward" or "downward" methods that may use lithography (generally), FTI (Film Transfer Imaging), 3D Printing technologies (e.g., photopolymer jet printing and multi-material photopolymer jet modeling), SLS (Selective Laser Sintering) or SLA (Stereolithography Apparatus). Examples of pattern generators may include Digital Light Processing technology (DLP) from Texas Instruments® or SXRD or LCD or LCOS or J-ILA from JVC, or LVT (Light Valve Technology) or GLV (Grating Light Valve) technology, in addition to a scanned pattern generators (e.g., a scanning laser).

The three-dimensional dental arch models described herein are generally prepared based on object data that defines the dimensions and shape of the model. The object data may take numerous different forms including STL (Stereo Lithography) files or CAD (Computer Aided Drafting) files commonly translated for rapid prototyping systems into formats such as SLC, CLI slice data files or voxelized data files for example. However, any input type may be used and converted internally to create the patterns used by the pattern generators or solidifiable material dispenser (in the case of photopolymer jet and multi-material photopolymer jet devices).

A voxelized bitmap may include or may be converted to a bitmap pattern (e.g., a two-dimensional representation) that further includes a binary energy state (e.g., ON/OFF), a grayscale value, and/or an exposure time for each pixel. The bitmap two-dimensional information may be a typical x/y location for a pixel (whether inherent to the file format or having specified locations). The grayscale value may be used to control the pattern generator's output to provide full intensity, no output, or variations in between. Where an exposure time per pixel is provided, the pattern generator may further "turn off" the output for the specified pixel after a certain amount of time has passed. When using a voxelized construction process, each voxel may have its own thickness which is controlled by the grayscale value and/or the exposure time. An energy state of OFF does not necessarily correspond to zero energy, but rather, may correspond to a level of energy that is insufficient to cause solidification of the solidifiable material used to make the three-dimensional object.

Referring to FIG. 1A, a first example of a dental arch model 40 in accordance with the present disclosure is depicted. The arch model 40 shown in FIG. 1A is a lower arch. However, upper arches may also be prepared in accordance with the techniques described herein. Arch model 40 includes a first leg 42 and a second leg 44 that meet at apex 48. Leg 42 includes a rear-most point 58 that is spaced apart from apex 48 in a first direction that defines an x-axis. Leg 44 includes a rear-most point 60 that is also spaced apart from apex 48 in a direction along the x-axis. The rear-most points 58 and 60 of legs 42 and 44 are spaced apart from one another in a direction that defines a y-axis that is perpendicular to the x-axis. Thus, each leg 42 and 44 projects away from apex 48 along both the x and y axes and has a generally curved shape in the x-y plane. Dental arch model 40 includes a plurality of teeth 70*a*-70*g* and replaceable teeth openings 71*a*-71*f*. The replaceable teeth openings 71*a*-71*f* are sized to receive models of teeth (also called "dies") that can be selectively inserted into and removed from the openings 71*a*-71*f*. The openings allow for the creation and evaluation of copings and crowns made in wax.

Figure 1B:
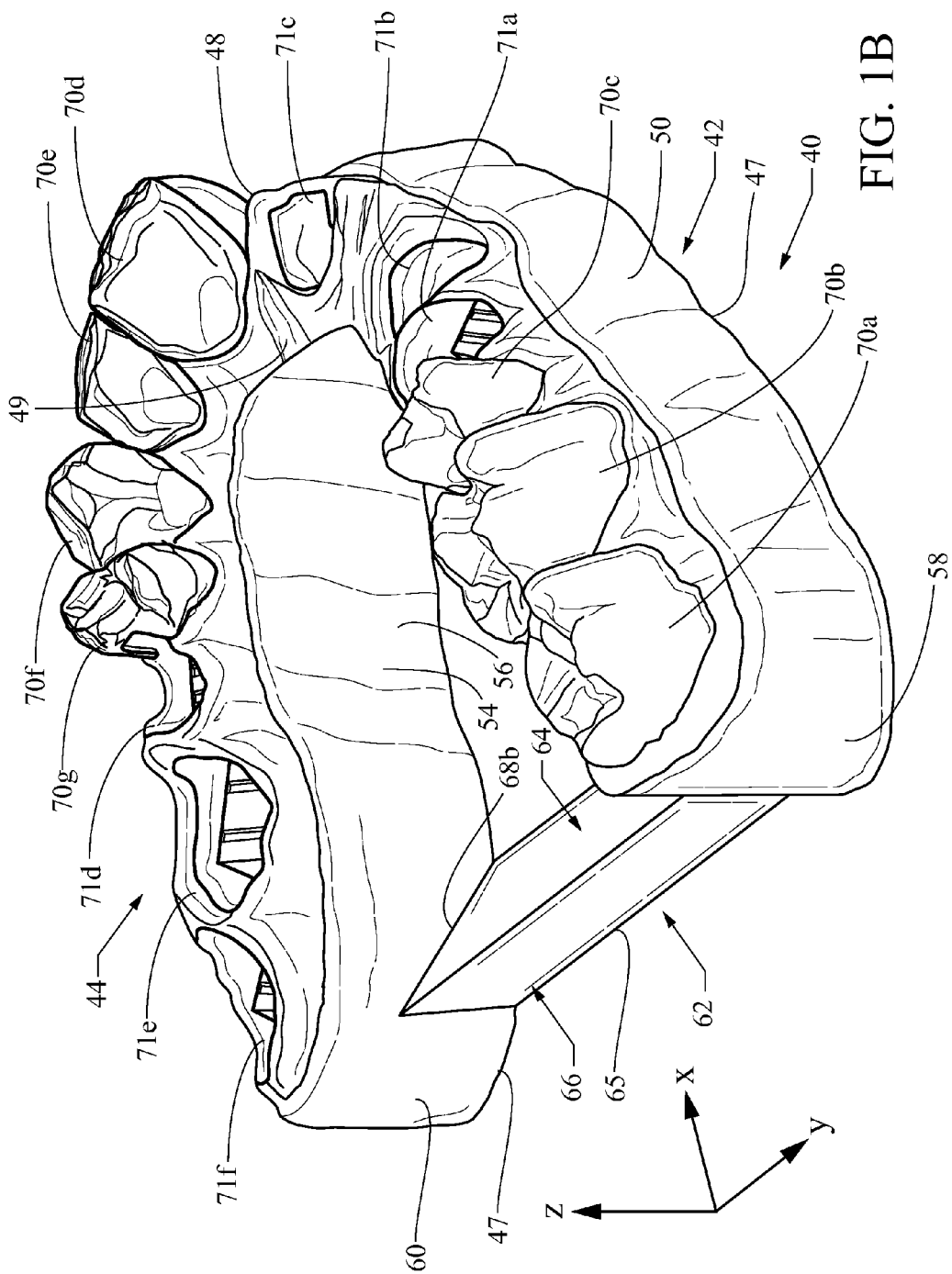
FIG. 1B is a perspective view of the dental arch model of FIG. 1A.

Referring to FIG. 1B, dental arch model 40 also includes an outer wall 50 that defines the outer perimeter of dental arch model 40. Outer wall 50 is spaced apart from inner wall 52 (FIG. 1B) in a direction along the x and/or y axis that varies with the location along the perimeter of outer wall 50. Dental arch model 40 also includes a base surface 47 and an upper surface 49. Teeth 70*a*-70*g* project away from upper surface 49 in a direction along the build (z) axis direction (FIG. 1B). The term "build axis" is used to refer to the direction in which the dental arch model 40 is progressively built during an additive manufacturing process of the type described previously. Base surface 47 includes a substantially planar surface that may be separated into sections by a plurality of fluid passageways (not shown in FIGS. 1A and B), as described further below. As best seen in FIG. 1B, upper surface 49 and base surface 47 are spaced apart from one another along the build (z) axis.

The legs 42 and 44 each include a free end that terminates in the rear-most points 58 (for leg 42) and 60 (for leg 44). Because the legs 42 and 44 are generally elongated and curved (when viewed along the z-axis direction) in shape, in many additive manufacturing processes the legs may separate from one another or otherwise experience deformation relative to the object data that defines the shape and dimensions of dental arch model 40. To minimize such effects, a connector 62 is provided which connects leg 42 to leg 44. In the particular example of FIG. 1A-B, the connector 62 includes three surfaces (64, 65, and 66) having lengths that extend along the y-axis direction, and two ends 68*a* and 68*b* that connect to the inner wall 52 of a respective one of the legs 42 and 44. Thus, connector end 68*a* is attached to the first leg inner wall 54, and connector 68*b* is connected to the second leg inner wall 56. In preferred examples, the connector 62 is integrally formed with the legs 42 and 44 of dental arch model. While the connector 62 is depicted as being solid in FIGS. 1A and 1B, it may alternatively include perforations, openings, or through-holes.

Connector lower surface 65 includes a substantially planar surface that may be separated into sections by a plurality of fluid passageways (not shown in FIGS. 1A and B), as described further below. In preferred examples connector lower surface 65 is substantially parallel to the plane defined by the x and y axes (i.e., the "x-y plane") and substantially co-planar with base surface 47. Rearward-facing connector surface 66 is generally perpendicular to the plane defined by the x and y axes (the "x-y plane"). Rearward-facing connector surface 66 may be configured for attachment to an articulator that is used to connect dental arch model 40 to an upper arch model to simulate movement and registration of a person's upper and lower teeth.

The connector 62 lacks a surface that is both substantially planar and substantially parallel to either connector lower surface 65 or base surface 47 along any more than two thirds of the length of the connector 62 along the y-axis direction. With respect to dental arch model 40 of FIGS. 1A and 1B in particular, the connector 62 lacks a surface that is both substantially parallel and substantially planar to connector lower surface 65 or base surface 47 along any portion of the y-axis length of connector 62. Rearward-facing surface 66 is substantially perpendicular to connector lower surface 65 along the length of the rearward-facing connector surface 66 in the y-axis direction. Forward facing connector surface 64 is sloped along its length along the y-axis and lies in a plane that intersects the x-y plane in which connector lower surface 65 lies. Thus, while the forward facing connector surface 64 is substantially planar along its length, it is not substantially parallel to the connector lower surface 65 along any portion of its length along the y-axis direction.

Figure 2A:
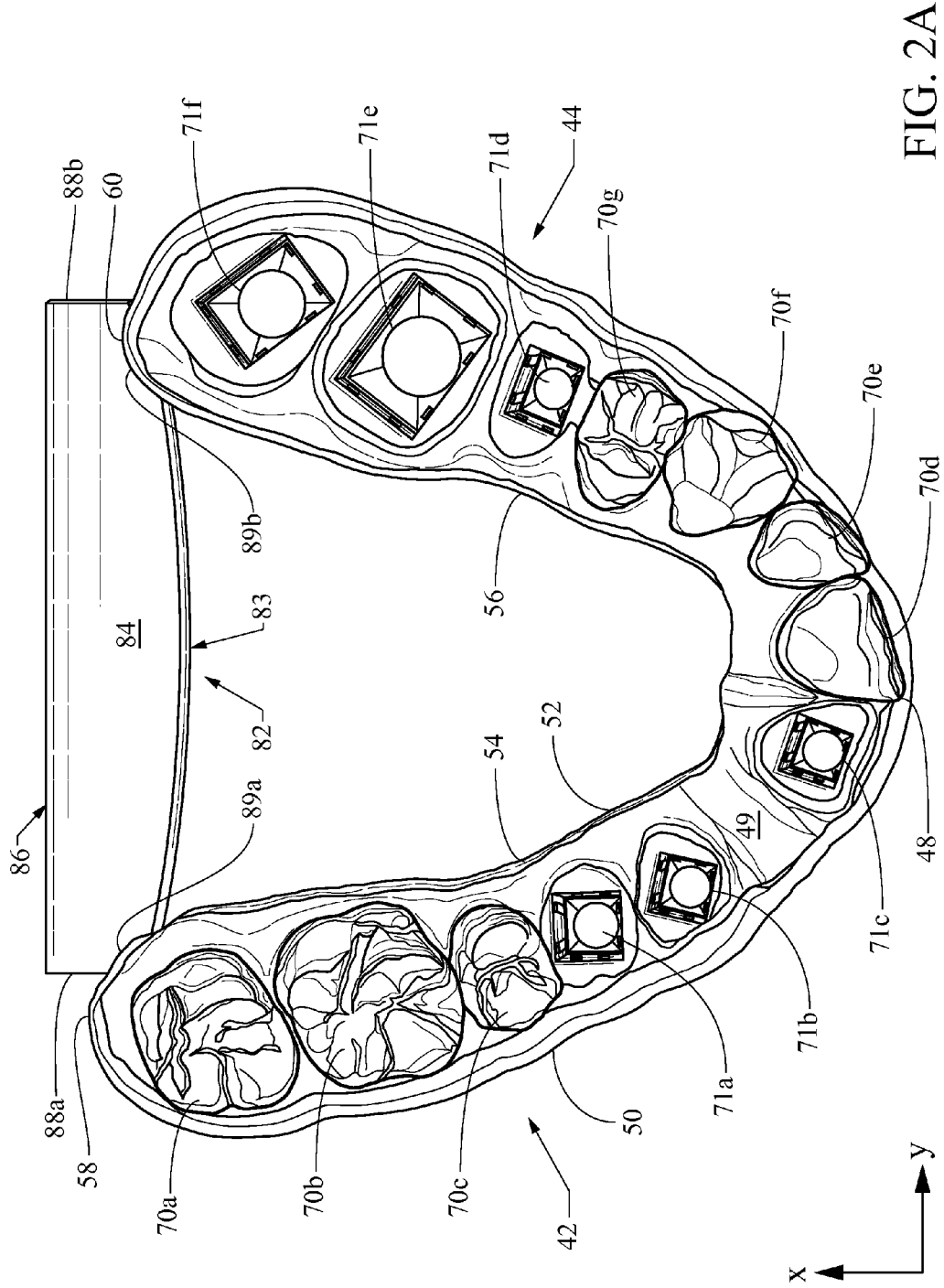
FIG. 2A is a top plan view of an embodiment of a dental arch model comprising a connector with a top surface that is sloped relative to the bottom surface of the model.
Figure 2B:
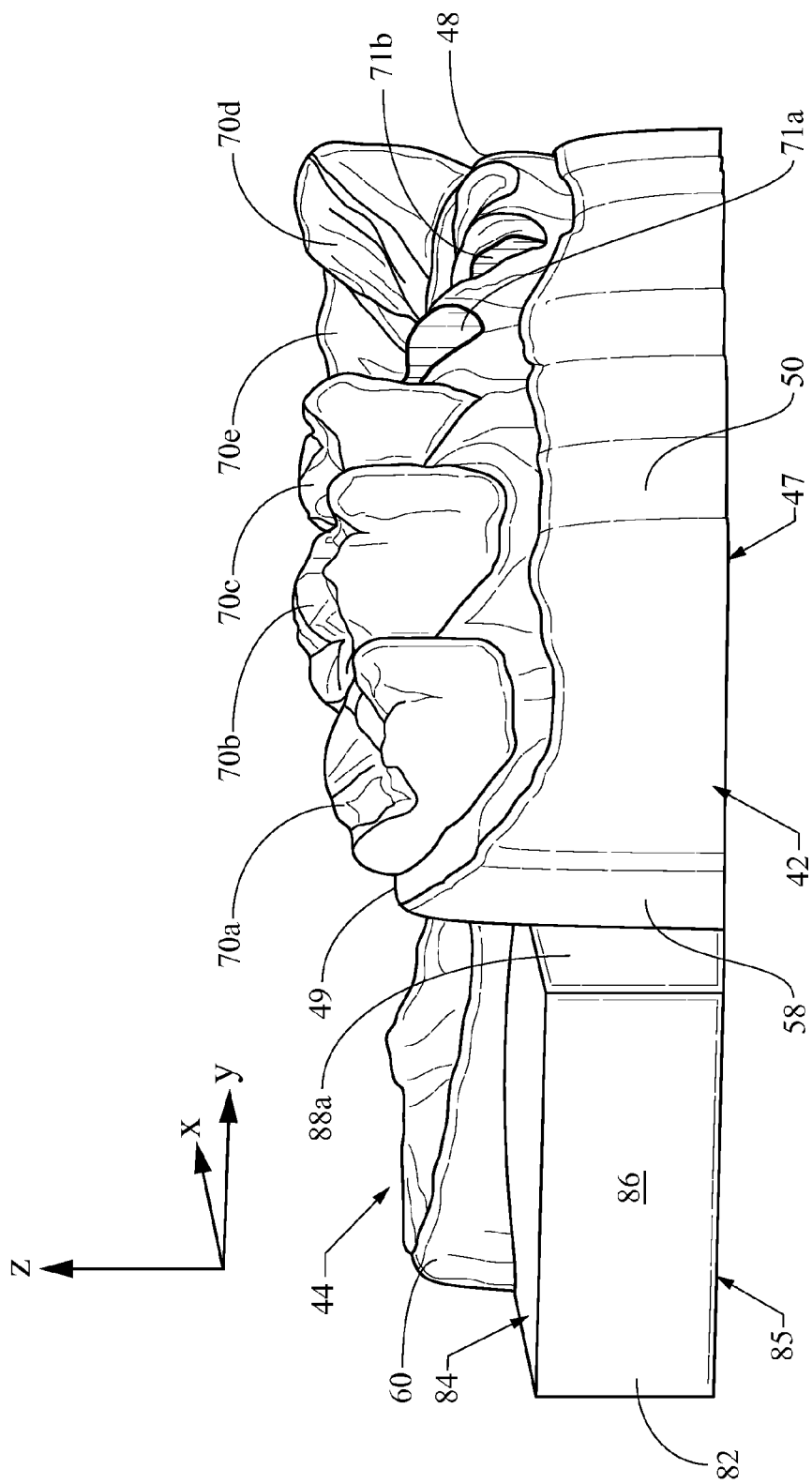
FIG. 2B is a perspective view of the dental arch model of FIG. 2A.

Referring to FIGS. 2A and 2B, another example of a dental arch model 40 in accordance with the present disclosure is depicted. The dental arch model 40 is configured similarly to the model 40 of FIGS. 1A and 1B, but includes a different connector 82. In the example of FIGS. 2A and 2B, connector 82 includes a connector lower surface 85 that includes a planar surface that may be separated into sections by a plurality of fluid passageways (not shown in FIGS. 2A and 2B). Connector 82 also includes a forward-facing surface 83 and a rearward-facing surface 86 that are spaced apart from one another along the x-axis direction and which each have a length along the y-axis direction. Connector 82 also includes ends 88a and 88b that are spaced apart from one another along the y-axis direction. The ends 88a and 88b and forward-facing surface 83 are shaped to include respective concave sections 89a and 89b (FIG. 2B) which are connected to corresponding convex sections formed in the first leg inner wall 54 and second leg inner wall 56, respectively.

Forward-facing surface 83 and rearward-facing surface 86 are substantially perpendicular to the x-y plane. While upper surface 84 is substantially planar, it is not substantially parallel to the connector lower surface 85 or base surface 47 of the legs 42 and 44 along any portion of its length. Instead, upper surface 84 is oriented obliquely with respect to connector lower surface 85 and the x-y plane. Preferred angles of orientation are at least about three (3) degrees. In the specific example of FIGS. 2A and 2B, the angle of orientation in the illustrated example is about ten (10) degrees.

Figure 3A:
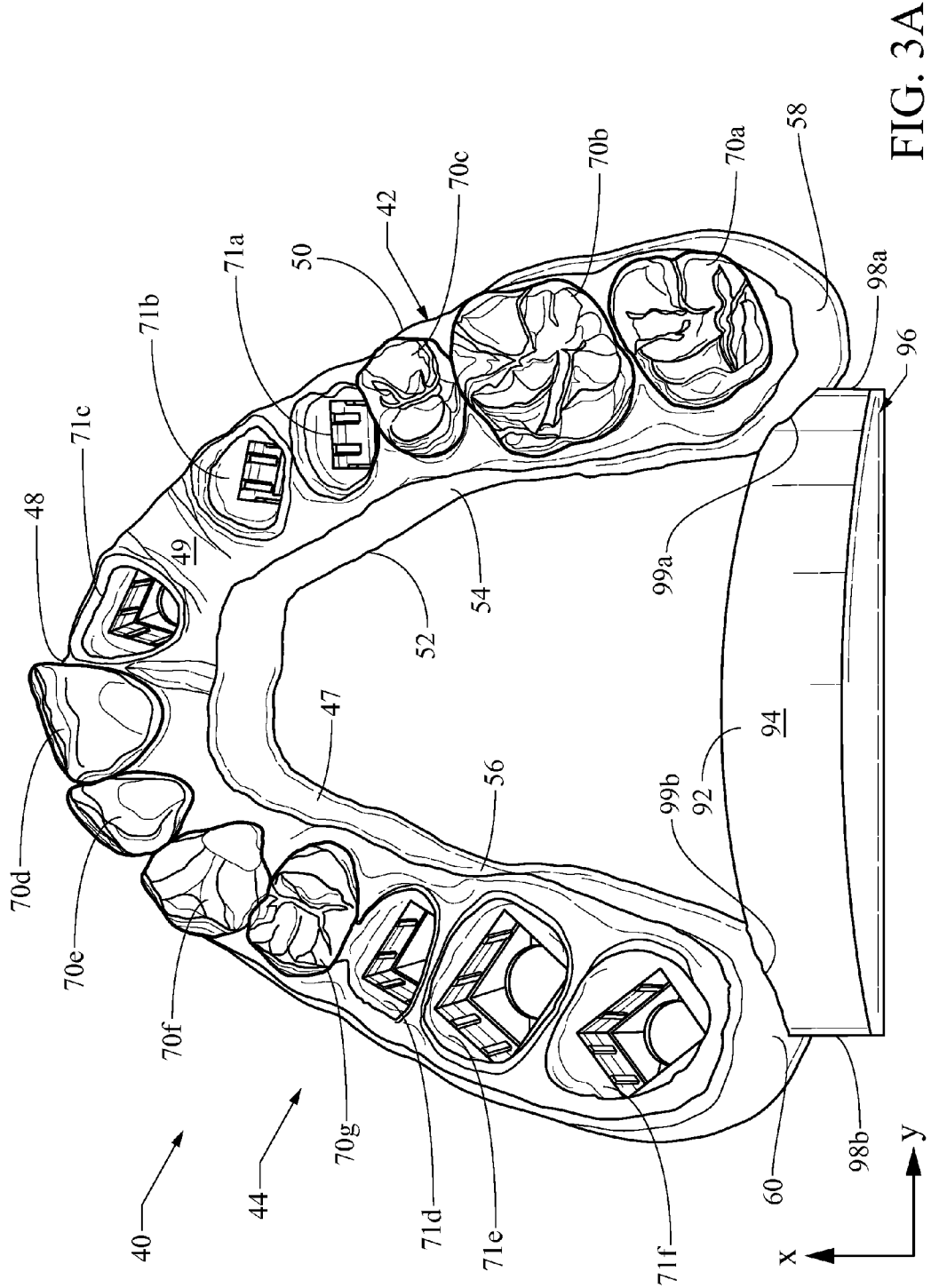
FIG. 3A is a top plan view of a dental arch model comprising a connector with a curved upper surface.
Figure 3B:
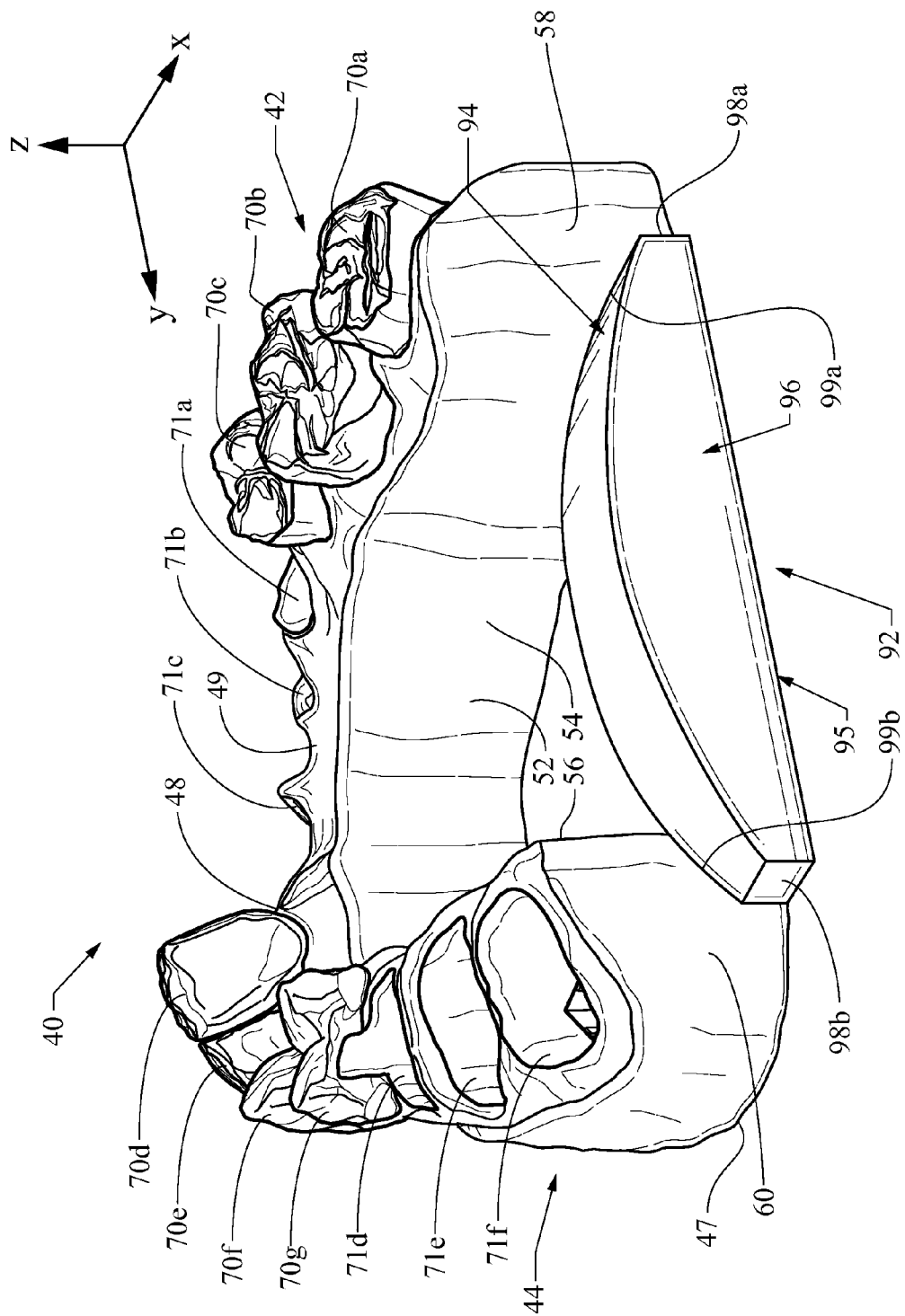
FIG. 3B is a perspective view of the dental arch model of FIG. 3A.

Referring to FIGS. 3A and 3B, a further example of a dental arch model 40 in accordance with the present disclosure is depicted. The legs 42 and 44 of dental arch model 40 are substantially similar to those depicted in FIGS. 1A-B and 2A-B. However, connector 92 has a different geometry.

Connector 92 includes a connector lower surface 95 that includes a substantially planar surface that may be separated into sections by a plurality of fluid passageways (not shown in FIGS. 3A and 3B). Connector 92 further includes a forward facing surface 93 (not shown in FIGS. 3A and 3B) that is spaced apart from rearward-facing surface 96 along the x-axis direction. Forward-facing surface 93 and rearward-facing surface 96 are substantially perpendicular to the x-y plane. Connector 92 also includes ends 98a and 98b which are spaced apart from one another along the y-axis direction. The ends 98a and 98b and forward-facing surface 93 are also shaped to create respective concave or angled sections 99a and 99b (FIG. 3A) that serve as connection points to first leg inner wall 54 and second leg inner wall 56.

In the example of FIGS. 3A and 3B, the upper surface 94 is neither substantially planar nor substantially parallel to connector lower surface 95 along any portion of the length of upper surface 94 along the y-axis direction. Instead, upper surface 94 has a curved profile when viewed along the x-axis. The upper surface 94 is spaced apart from connector lower surface 95 along the z-axis direction, but the extent of the spacing varies along the y-axis length of the connector 92. The spacing is at its minimum value at the portion of upper surface 94 that intersects ends 98a and 98b and is at its maximum value at the mid-point of the upper surface 94 along the y-axis direction.

Figure 4A:
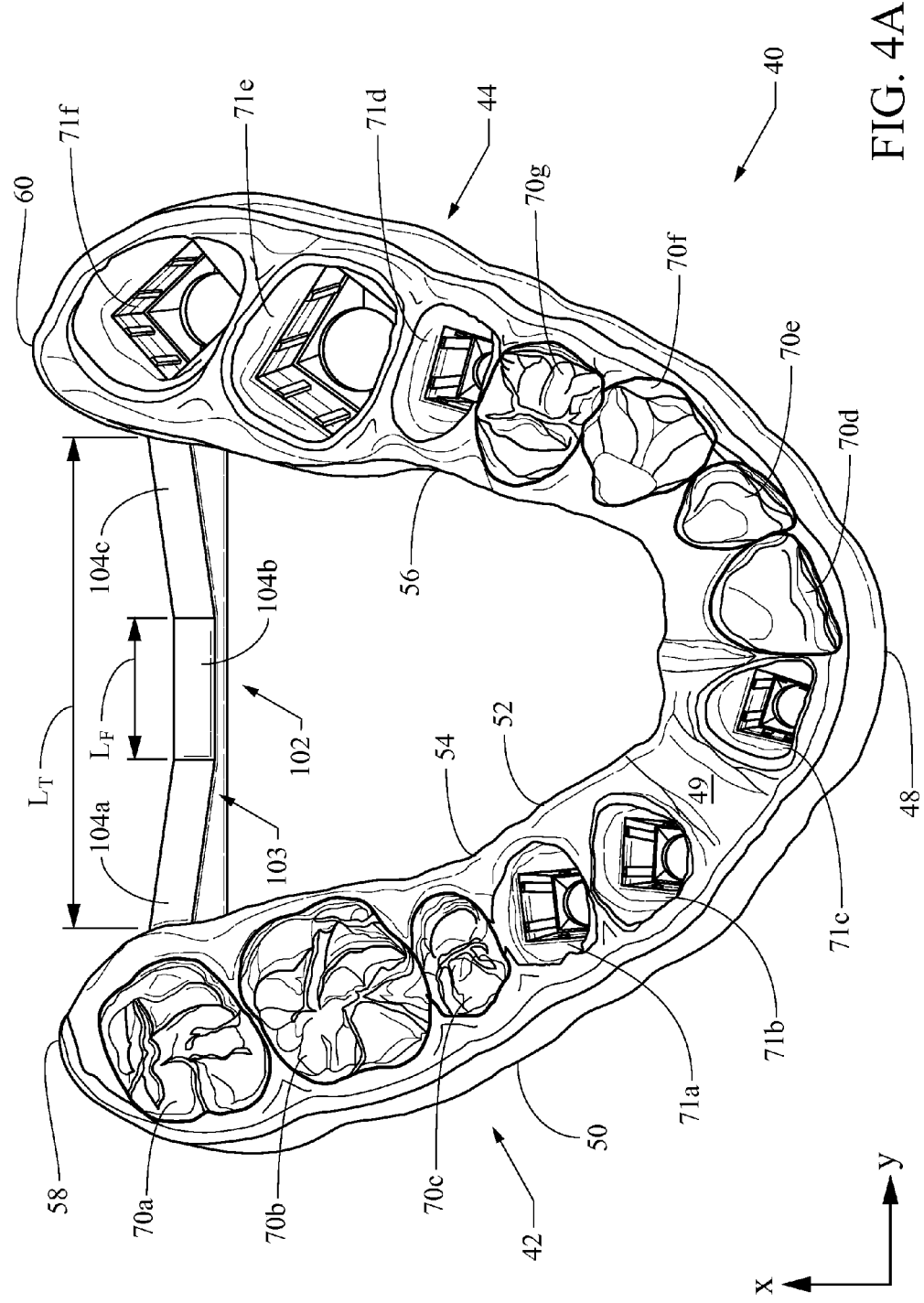
FIG. 4A is a top plan view of a dental arch model comprising connector with a non-quadrilateral, polygonal profile.
Figure 4B:
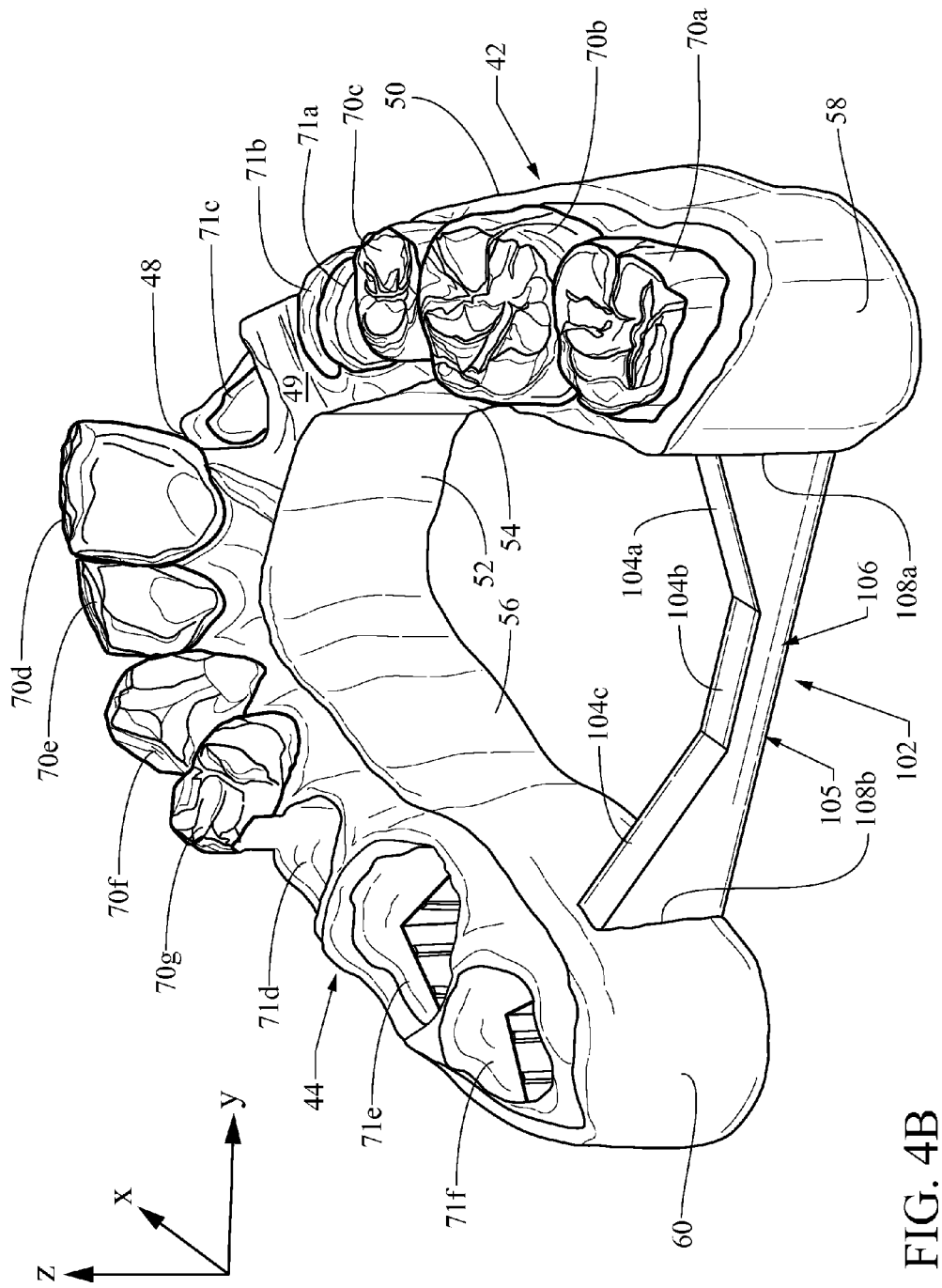
FIG. 4B is a perspective view of the dental arch model of FIG. 4A.

Referring to FIGS. 4A and 4B, a further example of a dental arch model 40 in accordance with the present disclosure is depicted. The legs 42 and 44 of dental arch model 40 are substantially similar to those depicted in FIGS. 1A-B, 2A-B, and 3A-3B. However, connector 102 has a different geometry.

The profile of connector 102 when viewed along the x-axis is polygonal, but not quadrilateral and has the appearance of a five-sided polygon. Connector 102 includes a connector lower surface 105 that includes a planar surface that may be separated into sections by a plurality of fluid passageways (not shown in FIGS. 4A and 4B). Forward-facing surface 103 is spaced apart from rearward-facing surface 106 in a direction along the x-axis. Forward-facing surface 103 and rearward-facing surface 106 are each substantially perpendicular to the x-y plane. Connector 102 also includes ends 108a and 108b that attach connector 102 to first leg inner wall 54 and second leg inner wall 56, respectively.

The upper surface of the connector 102 comprises three upper surface segments 104a, 104b, and 104c. Upper surface segment 104b is located between upper surface segments 104a and 104c along the y-axis direction. The upper surface segments 104a and 104c are substantially planar along their lengths along the y-axis direction. However, neither of them is substantially parallel to the connector lower surface 105. Instead, they each slope towards the connector lower surface 105 when moving along the y-axis and away from the particular inner wall 54 or 56 to which the surface segment 104a and 104c is connected. Thus, the upper surface segments 104a and 104c are spaced apart from connector lower surface 105 along their lengths, but the extent of the spacing varies along the y-axis.

Unlike the previous connectors 62, 82, and 92, the upper surface 104 of connector 102 includes a segment 104b that is both substantially parallel to connector lower surface 105 and substantially planar. However, the length of segment 104b ($L_F$) as measured along the y-axis direction is preferably no more than two thirds of the entire connector length $L_T$ as measured along the y-axis direction. In the particular example of FIGS. 4A-4B, $L_F$ is slightly less than one-third of $L_T$ as illustrated in FIG. 4A.

As discussed herein, a solidifiable material is a material that when subjected to energy, wholly or partially hardens. This reaction to solidification or partial solidification may be used as the basis for constructing the three-dimensional object, such as a dental arch model. Examples of a solidifiable material may include a polymerizable or cross-linkable material, a photopolymer, a photo powder, a photo paste, or a photosensitive composite that contains any kind of ceramic based powder such as aluminum oxide or zirconium oxide or ytteria stabilized zirconium oxide, a curable silicone composition, silica based nano-particles or nanocomposites. The solidifiable material may further include fillers. Moreover, the solidifiable material my take on a final form (e.g., after exposure to the electromagnetic radiation) that may vary from semi-solids, solids, waxes, and crystalline solids. In one embodiment of a photopolymer paste solidifiable material, a viscosity of between 10000 cP (centipoises) and 150000 cp is preferred.

When discussing a photopolymerizable, photocurable, or solidifiable material, any material is meant, possibly comprising a resin and optionally further components, which is solidifiable by means of supply of stimulating energy such as electromagnetic radiation. Suitably, a material that is polymerizable and/or cross-linkable (i.e., curable) by electromagnetic radiation (common wavelengths in use today include UV radiation and/or visible light) can be used as such material. In an example, a material comprising a resin formed from at least one ethylenically unsaturated compound (including but not limited to (meth)acrylate monomers and polymers) and/or at least one epoxy group-containing compound may be used. Suitable other components of the solidifiable material include, for example, inorganic and/or organic fillers, coloring substances, viscose-controlling agents, etc., but are not limited thereto.

When photopolymers are used as the solidifiable material, a photoinitiator is typically provided. The photoinitiator absorbs light and generates free radicals which start the polymerization and/or crosslinking process. Suitable types of photoinitiators include metallocenes, 1,2 di-ketones, acylphosphine oxides, benzyldimethyl-ketals, α-amino ketones, and α-hydroxy ketones. Examples of suitable metallocenes include Bis(eta 5-2,4-cyclopenadien-1-yl) Bis[2,6-difluoro-3-(1H-pyrrol-1-yl) phenyl]titanium, such as Irgacure 784, which is supplied by Ciba Specialty chemicals. Examples of suitable 1,2 di-ketones include quinones such as camphorquinone. Examples of suitable acylphosphine oxides include bis acyl phosphine oxide (BAPO), which is supplied under the name Irgacure 819, and mono acyl phosphine oxide (MAPO) which is supplied under the name Darocur® TPO. Both Irgacure 819 and Darocur® TPO are supplied by Ciba Specialty Chemicals. Examples of suitable benzyldimethyl ketals include alpha, alpha-dimethoxy-alpha-phenylacetophenone, which is supplied under the name Irgacure 651. Suitable α-amino ketones include 2-benzyl-2-(dimethylamino)-1-[4-(4-morpholinyl) phenyl]-1-butanone, which is supplied under the name Irgacure 369. Suitable α-hydroxy ketones include 1-hydroxy-cyclohexyl-phenyl-ketone, which is supplied under the name Irgacure 184 and a 50-50 (by weight) mixture of 1-hydroxy-cyclohexyl-phenyl-ketone and benzophenone, which is supplied under the name Irgacure 500.

Without wishing to be bound by any theory, it is believed that connectors with upper surfaces that are planar and parallel to the base 47 of dental arch model 40 along more than two-thirds of the connector length tend to cause distortion of the dental arch model 40 when manufactured using an additive rapid prototyping process of the type described previously. This effect is believed to be particularly pronounced in the case of certain classes of acrylic-based, cross-linked resins which in general are suitable for use in preparing dental arch models. Preferred solidifiable materials for use in preparing the dental arch models described herein comprise: (a) a photocurable component that is liquid at room temperature and which includes a photopolymerizable substance selected from the group consisting of monomers, oligomers, dendrimers and polymers and mixtures thereof, (b) at least one photoinitiator compound, and (c) at least one organic or inorganic color compound. The concentration of color compound can be adapted to go from essentially colorless to colored a photocurable composition. Without wishing to be bound by any theory, it is believed that the inclusion of a color compound reduces unwanted expansion of the solidified material relative to the dimensions dictated by the dental arch model object data. Such expansion may, for example, cause areas of solidified material to "bleed" into the openings 71a-71f and prevent the insertion of removable teeth models.

The preferred photocurable compositions for preparing the dental arch models 40 described herein are those in which the free radically curable component contains: di(meth)acrylates, tri(meth)acrylates or penta(meth)acrylates. Suitable examples of di(meth)acrylates are the di(meth)acrylates of cycloaliphatic or aromatic diols such as 1,6-hexadiol diacrylate, 1,4-dihydroxymethylcyclohexane, 2,2-bis(4-hydroxycyclohexyl)propane, bis(4-hydroxycyclohexyl)methane, hydroquinone, 4,4'-dihydroxybi-phenyl, Bisphenol A, Bisphenol F, Bisphenol S, ethoxylated or propoxylated Bisphenol A, ethoxylated or propoxylated Bisphenol F or ethoxylated or propoxylated Bisphenol S. Di(meth)acrylates of this kind are known and some are commercially available from Sartomer, Surface Specialties, Coagins, etc.

The radical photoinitiators are preferably selected to initiate polymerization of materials including acrylate, methacrylate, norbonyl and styryl functional groups. Such compounds are benzoin, benzoin ethers, benzoin acetate, acetophenones, benzil, bezil ketals, antraquinones, triphenylphosphine, benzophenones, and 1-hydroxyphenyl ketones. The preferred radical photoinitiators are 2,2-dialkoxybenzophenones, 1-hydroxyphenyl ketones, 2-hydroxy-2,2-dimethylacetophenone, benzil dimethylketal and camphorquinone, which are available from BASF and Rahn.

In certain examples, the color compounds are employed to give a color to essentially colorless photocurable composition. Such compounds include inorganic and organic dyes and pigments, for example: cadmium sufloselenide, 1-(2,4-dinitrophenylazo)-2-naphtol, chromium complexes of azo dyes, potassium cobaltinitrite, cadmium sulfide, barium sulfate, titanium dioxide etc. It is believed that using the foregoing preferred solidifiable materials to prepare dental arch models yields models with dimensional stability of at least four weeks following post curing treatment in a light box. In addition, the use of the color compounds is believed to allow removable teeth (referred to as "dies") to be repeatedly inserted into and withdrawn from openings 71a to 71f more than twenty times without wall degradation or without the walls defining the openings 71a to 71f becoming tacky. Without wishing to be bound by any theory, it is believed that color compounds filter light received by the solidifiable material and thereby reduce light scattering and undesirable polymerization that can cause bleeding of the solidified material into the openings 71a to 71f.

In certain examples, the color compound comprises at least about 10 percent, preferably at least about 15 percent, and more preferably at least about 18 percent by weight of the total solidifiable material composition. In the same or other examples, the color compound comprises no more than about 30 percent, preferably not more than about 25 percent, and more preferably not more than about 22 percent by weight of the total solidifiable material composition. In one example, an orange dye color compound called Orange 10 supplied by Ming-Zu Chemical of China is added to an HTM 140 IV material (that includes an acrylic photocurable component and a photoinitiator) in an amount of 0.25 kg/kg HTM 140 IV. HTM 140 IV is supplied by Envisiontec, Inc. of Dearborn, Mich. Orange 10 corresponds to Solvent 54 (CAS 12237-30-8) which is also known by the name Hydrogen bis[2,3-dioxobutyranilide 2-[(2-hydroxy-5-nitrophenyl) hydrazonato(2-)]]cobaltate(III). The color compound is preferably selected to be compatible with the monomers used to prepare the solidifiable material.

A method of making a dental arch model in accordance with the foregoing disclosure will now be described. In accordance with the method, a build platform is provided on which the arch model will be built. The build platform includes a surface on which the dental arch model is built and defines a reference location along the build (z) axis. In preferred examples, the dental arch model is progressively built along the build-axis in a direction away from the build platform. In accordance with one method, object data of the type described previously is provided and is used to guide the process of building the dental arch model. Solidifiable material is progressively added to a previously solidified section of the dental arch and is then solidified. In certain examples, such as those involving spatial light modulators such as digital light projectors, LED arrays, or liquid crystal display matrices, solidification energy is projected in a series of two-dimensional patterns, each of which corresponds to a location along the build axis as the dental arch model is built. In laser scanning systems, solidification energy is "drawn" or traversed with a point source to create a pattern that corresponds to a location along the build axis. In linear scanning systems, solidification energy is transmitted by a solidification energy source such as a laser diode to a scanning device, such as a rotating polygonal mirror, which then deflects the received solidification energy in a plurality of adjacent linear segments across an exposed surface of solidifiable material. In other examples, such as those involving photopolymer jet printing or multi-material photopolymer jet printing, solidifiable material is deposited in a pattern that corresponds to a location along the build (z) axis and is then subjected to solidification energy to solidify the deposited pattern. Thus, in some cases the solidification energy pattern dictates the shape of a portion of the dental arch model (i.e., the portion at a given build (z) axis location), while in other cases, the dispensed solidifiable material pattern dictates the shape of a portion of the dental arch model (i.e., the portion at a given build (z) axis location). In certain examples, a computing device and one or more controllers will control the supply of solidifiable material and solidification energy and/or the movement of the build platform.

As mentioned previously, in many additive rapid prototyping processes, the object of interest is built on removable supports which connect the object to the build platform. However, the use of supports results in excess consumption of solidifiable material, prolonged build times, and in many cases, disruption or distortion to the base surface 47 of the dental arch model and the lower surface (65, 85, 95, and 105) of the connector (62, 82, 92, and 102). However, the elimination of supports may also lead to such disruption or damage to the base surface 47 and/or connector lower surfaces 65, 85, 95, and 105. Without supports the base surface 47 of the dental arch model 40 and the connector lower surface (65, 85, 95, 105) will solidify in contact with the build platform, which also can result in damage to the dental arch model 40 when it is removed. In addition, each of the dental arch models 40 depicted in FIGS. 1A-4B includes an enclosed or "trapped" volume defined between the forward-facing surface (64, 83, 93, and 103) of the connector (62, 82, 92, and 102) and the inner wall 52 of the dental arch model. This enclosed volume can trap solidifiable material which then solidifies. The trapped solidified material may exert pressure on the internal wall 52 and can result in distortion of the part dimensions. The trapped volume can easily be eliminated with supports, but may become a problem if support-less dental arch models are desired. The creation of trapped volumes may become especially pronounced in those additive processes in which the build platform is progressively immersed in volume of the solidifiable material during the object build process.

To facilitate the creation of support-less dental arch models, a plurality of fluid passageways may be provided to place the enclosed volume between connectors 62, 82, 92, and 102 and dental arch model inner wall 52 in fluid communication with the area exterior to the outer wall 50 of dental arch model 40. In certain examples, the fluid passageways extend from the inner wall 52 to the outer wall 50 of the dental arch model 40. In the same or other cases, fluid passageways may extend through connector 62, 82, 92, and 102. In certain preferred examples, the fluid passageways are also created to reduce the contact surface area between the dental arch model base 47 and the build platform. In the same or other cases, the fluid passageways may be created to reduce the contact surface area between the connector lower surface (65, 85, 95, and 105) and the build platform. In additional preferred examples, the fluid passageways are provided when the dental arch model 40 is built using a process wherein the build platform is progressively immersed in a volume of solidifiable material in the build axis direction as the dental arch model 40 is built.

Figure 7:
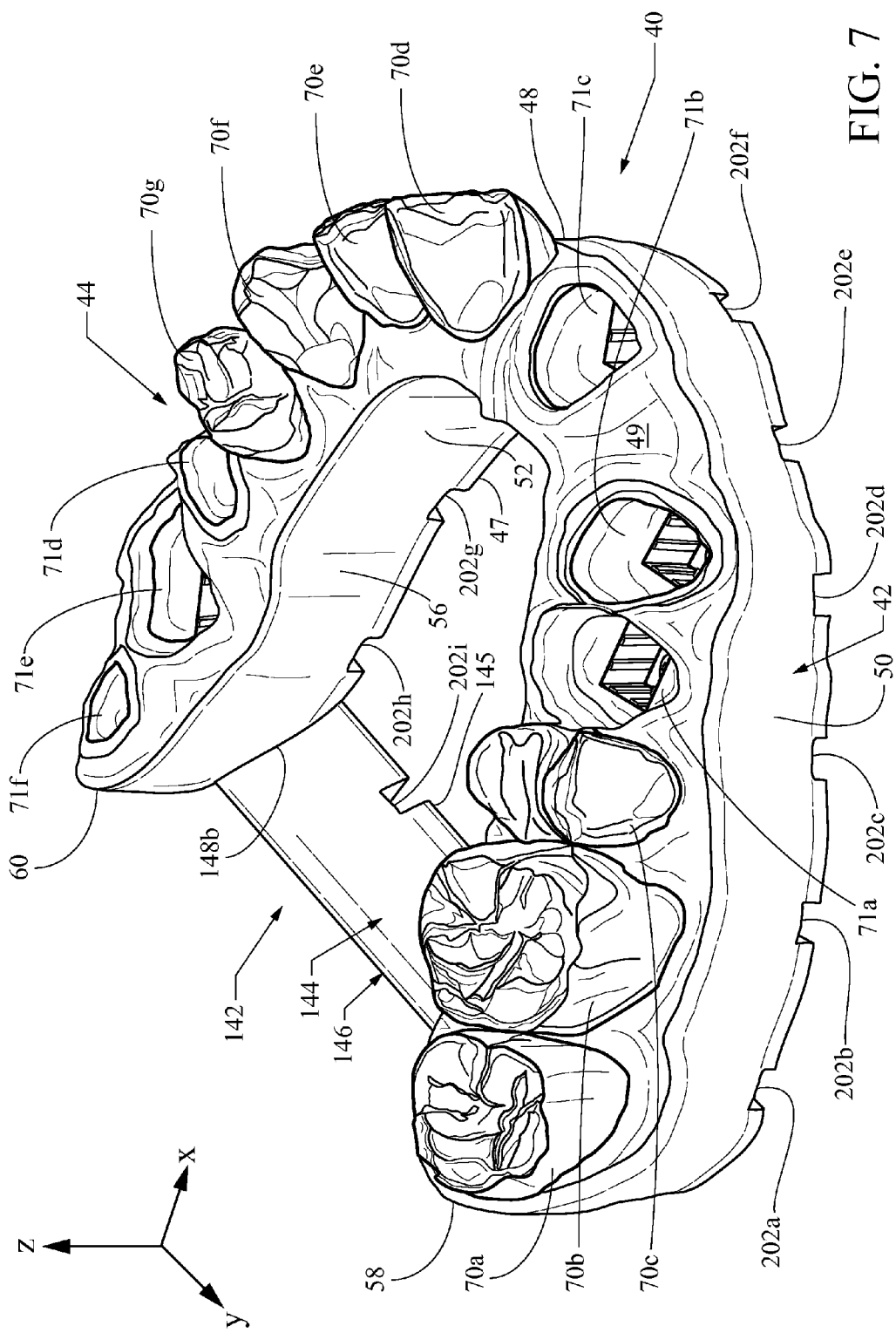
FIG. 7 is a photograph of a dental arch model comprising a plurality of fluid passageways and a prism-shaped connector.

Referring now to FIG. 7, a photograph of a dental arch model 40 is provided which is similar to the dental arch model 40 of FIGS. 1A and 1B. However, in FIG. 7 the dental arch model includes a plurality of fluid passageways 202a-202i extending around the perimeter of the dental arch model 40. Fluid passageways 202a-202h extend from the outer wall 50 to the inner wall 52 of the dental arch model, placing the area outside of the outer wall 50 in fluid communication with the area inside of the inner wall 52. In preferred examples, and as shown in FIG. 7, the fluid passageways 202a-202h are open channels defined by a recessed area formed in the base surface 47 of dental arch model 40. In other words, the channel is not bounded on all sides by the solidified material used to form the dental arch model 40. Instead, the build platform acts as one of the channel sides. This open channel configuration reduces the surface area of base surface 47 that is in contact with the build platform, which reduces the overall adhesive force of the dental arch model 40 to the build platform, thereby facilitating the removal of the model 40 from the build platform.

The fluid passageways 202a-202h are preferably sized to ensure that accumulated fluid within the enclosed area between connector 144 and inner wall 52 does not exceed a desired level. In certain preferred examples, each fluid passageway 202a-202h has a volume of at least about 30 mm$^3$, preferably at least about 40 mm$^3$, and more preferably at least about 50 mm$^3$. In the same or other examples, each fluid passageway has a volume of not more than about 80 mm$^3$, preferably not more than about 70 mm$^3$, and even more preferably not more than about 60 mm$^3$. In one example, the fluid passageway volume is about 56.25 mm$^3$.

In the same or other examples, each fluid passageway 202a-202h is linear. In certain preferred examples, each fluid passageway 202a-202h is linear and has a width perpendicular to the direction of fluid flow that is at least about 1.5 mm, preferably at least about 2.0 mm, and more preferably at least about 2.2 mm. In the same or other examples, each fluid passageway 202a-202h is linear and has a width that is no more than about 3.5 mm, preferably no more than about 3.0 mm, and even more preferably no more than about 2.7 mm.

In the same or other examples, each fluid passageway 202a-202h is linear and has a height (in the z-axis direction) that is at least about 1.5 mm, preferably at least about 2.0 mm, and more preferably at least about 2.4 mm. In the same or other examples, each fluid passageway 202a-202h is linear and has a height (in the z-axis direction) that is no more than about 4.5 mm, preferably no more than about 4.0 mm, and more preferably no more than about 3.4 mm.

In the same or other examples, each fluid passageway 202a-202h is linear and has a length (in the direction parallel to fluid flow) of at least about 5 mm, preferably at least about 6 mm, and more preferably, at least about 7.0 mm. In the same or other examples, each fluid passageway 202a-202h is linear and has a length (in the direction parallel to fluid flow) that is not more than about 9 mm, preferably not more than about 8.5 mm, and more preferably not more than about 8.0 mm. In one specific example, fluid passageways 202a-202h have a length (in the direction parallel to fluid flow) of about 7.5 mm, a width (in a direction perpendicular to fluid flow) of about 2.5 mm, and a height (in the build (z) axis direction) of about 3 mm. In certain preferred examples, connector 142 also includes a fluid passageway 202i (or multiple passageways). The preferred dimensions of the fluid passageway 202i are the same as those set forth above for fluid passageways 202a-202h.

Connector 142 is similar to connector 62 (FIGS. 1A and 1B) with the exception of the fluid passageway 202i provided in connector 142. Connector 142 includes rearward-facing surface 146, a lower surface 145, and a forward-facing surface 144. The forward-facing surface 144 is generally planar long the length of connector 142 in the y-axis direction, but is not substantially parallel to connector lower surface 145 at any location along the length of connector 142. Connector ends 148a and 148b connect the connector 142 to dental arch model legs 42 and 44, respectively.

Figure 5:
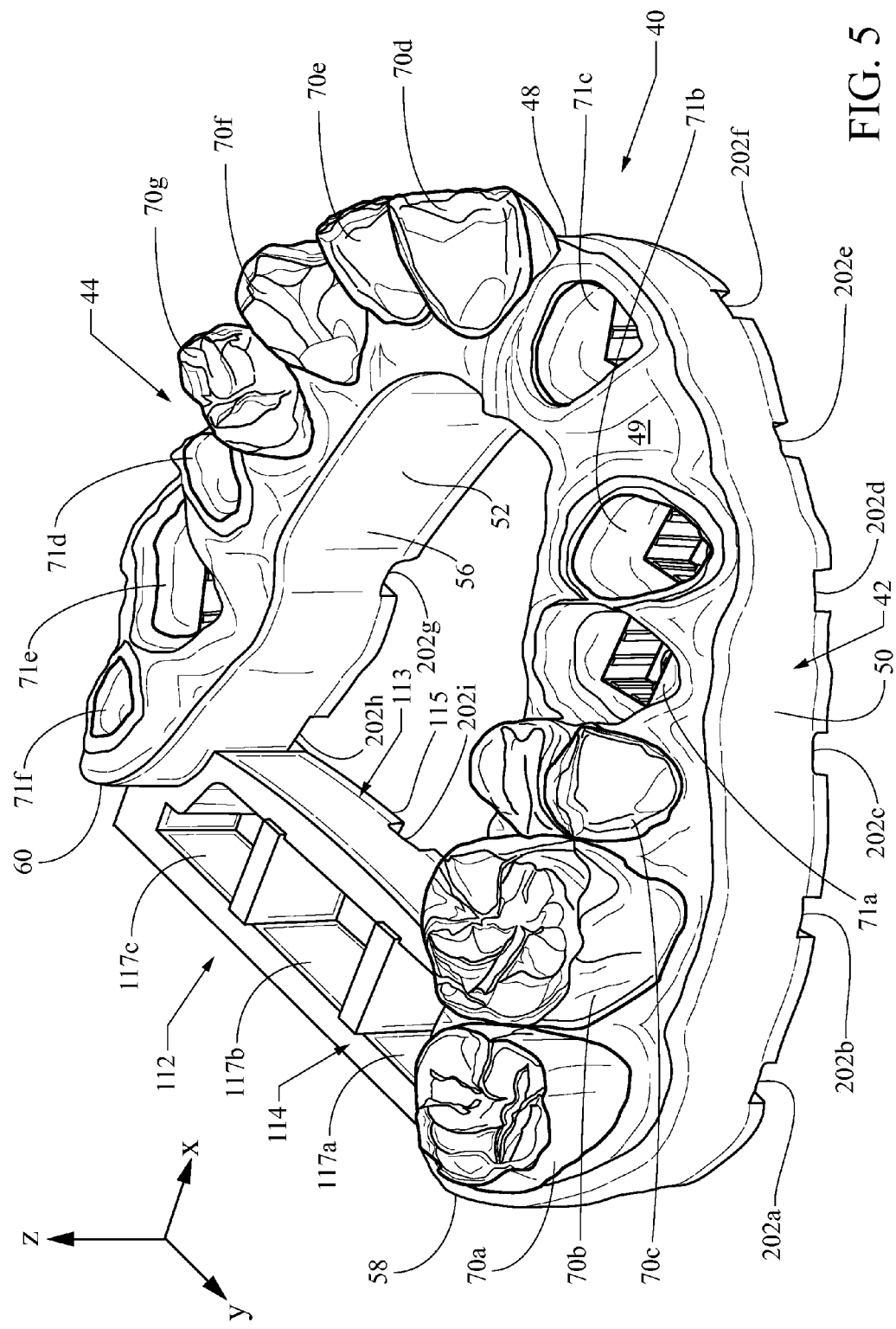
FIG. 5 is a photograph of a dental arch model comprising a plurality of fluid passageways and a partially hollow connector with a flat top surface.

Referring now to FIG. 5, a dental arch model 40 is shown which includes a plurality of fluid passageways 202a-202h. The fluid passageways 202a-2092d are configured similarly to fluid passageway 202a-202h of FIG. 7. However, connector 112 is not configured similarly to any of connectors 62, 82, 92, or 102. Connector 112 includes a lower surface 125 that includes a substantially planar surface separated into sections by channel 202i. In addition, connector 112 includes a plurality of hollow compartments 117a-117c. Connector 112 includes a forward-facing surface 113 and a rearward-facing surface 116 (not shown in the figure) which are spaced apart from one another along the x-axis direction. Fluid passageway 202i extends from forward-facing surface 113 to rearward facing surface 116 (not shown). Connector 112 includes an upper surface 114 that is substantially planar and substantially parallel to lower connector surface 115 and dental arch model base surface 47 along the length of connector 112 in the y-axis direction. Thus, while dental arch model 40 of FIG. 5 beneficially allows fluid to flow from the enclosed space defined by connector 122 and inner wall 52, it may cause distortion of the dental arch model due to the shape and geometry of upper surface 124.

Figure 6:
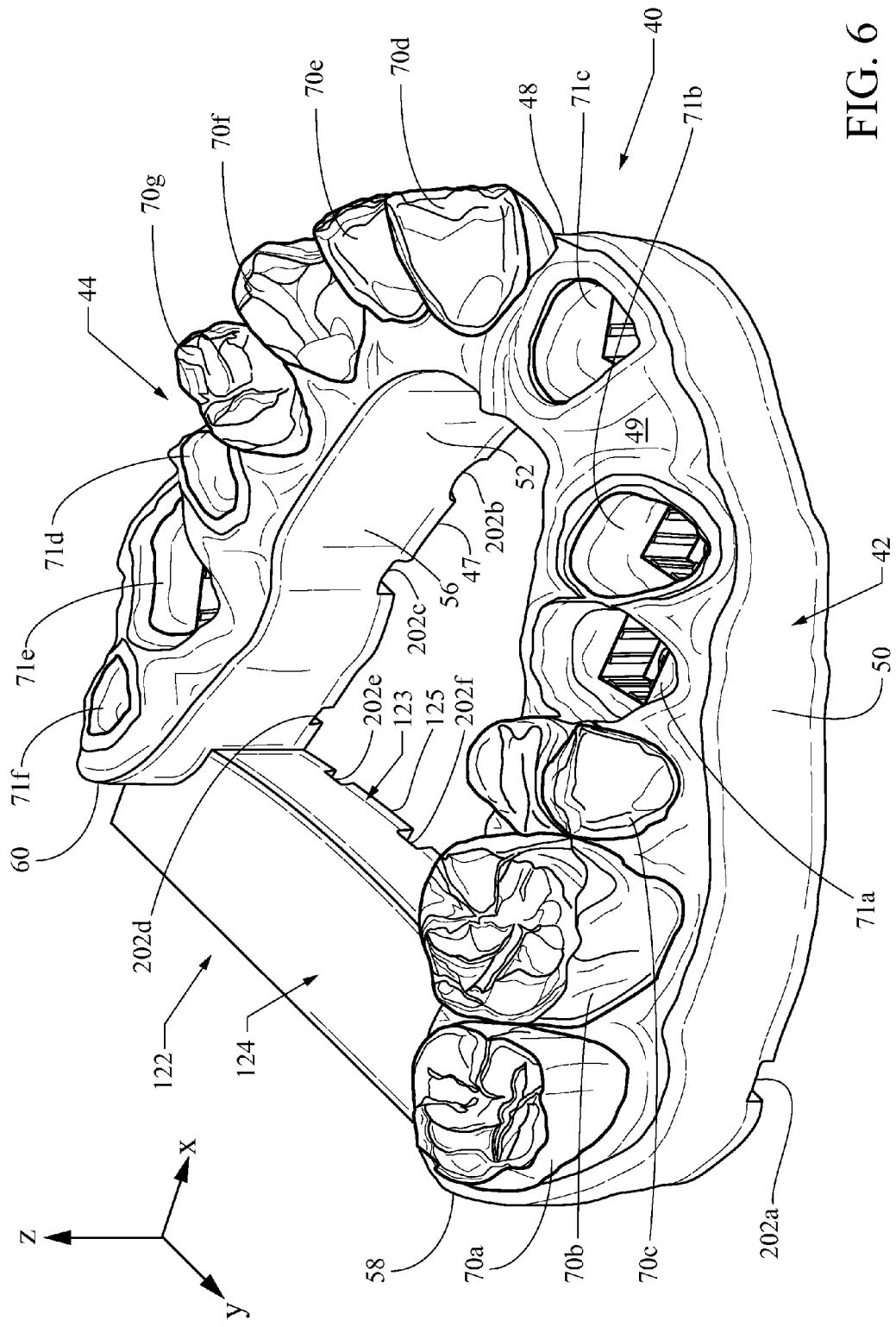
FIG. 6 is a photograph of a dental arch model comprising a solid connector with a plurality of fluid passageways and a flat top surface.

Referring now to FIG. 6, a dental arch model 40 is shown which includes a plurality of fluid passageways 202a-202d. The fluid passageways 202a-202d are configured similarly to fluid passageways 202a-202h of FIG. 7. However, connector 122 is not configured similarly to any of connectors 62, 82, 92, or 102. Connector 122 includes a lower surface 125 that includes a substantially planar surface separated into sections by fluid passageways 202e and 202f. Connector 122 also includes a forward-facing surface 123 and a rearward-facing surface 122. Ends 128a and 128b are spaced apart from one another along the length (y-axis) direction of connector 122 but are not shown in FIG. 6.

Connector 122 includes an upper surface that is substantially planar along its length and which is substantially parallel to the base surface 47 of dental arch model and connector lower surface 125. Thus, while the dental arch model 40 of FIG. 6 beneficially allows fluid to flow from the enclosed space defined by connector 122 and inner wall 52, it may cause distortion of the dental arch model due to the shape and geometry of upper surface 124.

The fluid passageways 202a-202i may have lengths (in the direction of fluid flow) that define a variety of angles relative to the x and y axes. In certain examples, the fluid passageways 202a-202i are parallel to one or the other of the x and y axes. In other examples, at least some of the fluid passageway s 202a-202i are oriented at an angle relative to each of the x and y axes. In certain preferred examples, at least some of the fluid passageways 202a-202i are oriented at substantially equal angles with respect to each of the x and y axes. Without wishing to be bound by any theory, it is believed that such an angular orientation reduces the forces of adhesion between the dental arch model 40 and the build platform when the model 40 is removed therefrom.

In certain examples, dental arch model 40 is configured with the lengths (in the direction of fluid flow) of certain of the fluid passageways 202a-202i oriented at an angle relative to each of the x and y axes. In accordance with such examples, the dental arch model 40 is removed by inserting a spatula with its leading edge perpendicular to the channel length and with its handle length parallel to the channel length. It is believed that this removal technique reduces the likelihood of damage to the dental arch model 40 and in particular to the base surface 47 thereof.

In certain preferred methods of making dental arch models 40, the arch model 40 is built by progressively solidifying a solidifiable material in a build axis direction to solidify the dental arch in direct contact with the build platform. In the same or other examples, the step of progressively solidifying the solidifiable material in the build axis direction comprises immersing the build platform into a volume of the solidifiable material in increments of no more than about 50 microns and supplying solidification energy to an exposed surface of the solidifiable material at each increment. It is believed that at increments of 50 microns or less, the use of connectors with upper surfaces that are flat and planar along more than two-thirds of the connector's length causes distortion of the dental arch model 40 in the x-y plane and also causes an unwanted change in the effective depth of solidification in the build (z) axis direction following the solidification of the upper surface of the connector.

EXAMPLES

Comparative Example

The dental arch model 40 depicted in FIG. 5 is built using an ULTRA three-dimensional printer supplied by Envisiontec, Inc. of Dearborn, Mich. The arch model is constructed using an HTM 140 IV acrylic resin solidifiable material supplied by Envisiontec, Inc. A color compound (Orange Dye 10 supplied by Ming-Zu Chemical) is added to the HTM 140 IV resin in an amount of 0.25 g/kg HTM 140 IV. Voxel data representative of the dental arch model 40 is supplied with a maximum voxel thickness of 50 microns.

The part build proceeds normally until the last voxel layer of upper surface 114 of connector 112 is reached. Following post-curing, the dental arch model is measured and compared to the corresponding object data using a magnification of 150×. The measurements indicate that the as-built dental arch model 40 begins to deviate from the voxel data by an amount of between 50 and 70 microns in the x-y plane immediately above (in the build axis direction) the upper surface 114 of connector 112. In FIG. 5 the shift in the x-y plane can be seen as a groove running along the inner wall 52 of the dental arch model 40 and in the inner surfaces of openings 71b and 71c (as indicated by arrows). The distances between voxel lines on the part are also measured using a magnification of 150×. The voxel lines beginning immediately after the last voxel layer of the upper surface 114 deviate from the specified value of 50 microns by values ranging from 25% to 150% of the 50 micron value. The maximum cured voxel thickness begins to return to the 50 micron value after several additional voxel layers. Similar results are observed building the dental arch model 40 of FIG. 6 with the same material and voxel thickness.

Example

The dental arch model 40 depicted in FIG. 7 is built using an ULTRA three-dimensional printer supplied by Envisiontec, Inc. of Dearborn, Mich. The arch model is constructed using an HTM 140 IV acrylic resin solidifiable material supplied by Envisiontec, Inc. A color compound (Orange Dye 10) is added to the HTM 140 IV resin in an amount of 0.25 g/kg HTM 140 IV. Voxel data representative of the dental arch model 40 is supplied with a maximum voxel thickness of 50 microns. Following post-curing, the dental arch model is measured and compared to the corresponding object data using a magnification of 150×. There is no appreciable deviation in the x-y plane even above the upper-most voxel layer of connector 142. In addition, the measured voxel layer thickness does not deviate appreciably from the 50 micron specification even above the upper-most voxel layer of connector 142.

The present invention has been described with reference to certain exemplary embodiments thereof. However, it will be readily apparent to those skilled in the art that it is possible to embody the invention in specific forms other than those of the exemplary embodiments described above. This may be done without departing from the spirit of the invention. The exemplary embodiments are merely illustrative and should not be considered restrictive in any way. The scope of the invention is defined by the appended claims and their equivalents, rather than by the preceding description.

What is claimed is:

1. A method of making a support-less dental arch model, comprising:
   providing a build platform; and
   progressively solidifying a solidifiable material in a build axis direction to solidify a dental arch model in direct contact with the build platform, wherein the dental arch model includes inner and outer surfaces with a plurality of fluid passageways extending from the inner surface to the outer surface, and further comprises a base surface and an upper surface spaced apart in a first direction along a first axis, first and second legs, and
   a connector having a length defining a second axis, a lower surface substantially parallel to the base, a first end connected to the first leg, and a second end connected to the second leg, wherein the connector lacks a second surface that is both parallel to the lower surface and substantially planar along more than two thirds of the connector length.

2. The method of claim 1, wherein the connector has three surfaces extending along the second axis, including the lower surface.

3. The method of claim 1, wherein the connector has an upper surface spaced apart from the lower surface in the first direction, and the upper surface is not substantially planar along more than two thirds of the connector length.

4. The method of claim 1, wherein the connector has an upper surface spaced apart from the lower surface in the first direction, and the upper surface is not substantially parallel to the base along more than two thirds of the connector length.

5. The method of claim 1, wherein the connector lacks a surface that is both parallel to the base and substantially planar along any portion of the connector length.

6. The method of claim 1, wherein the connector includes an upper surface spaced apart from the lower surface in the first direction, and the upper surface is curved.

7. The method of claim 1, wherein the connector includes a surface that is oriented obliquely with respect to the lower surface.

8. The method of claim 1, wherein the connector is prism-shaped.

* * * * *